United States Patent
Destaillats et al.

(10) Patent No.: US 11,261,401 B2
(45) Date of Patent: Mar. 1, 2022

(54) SYNTHESIS OF 1,3-OLEIN-2-PALMITIN (OPO)

(71) Applicant: SOCIETE DES PRODUITS NESTLE S.A., Vevey (CH)

(72) Inventors: Frederic Destaillats, Servion (CH); Francesca Giuffrida, Mezieres (CH); Amaury Patin, Lausanne (CH)

(73) Assignee: Societe des Produits Nestle S.A., Vevey (CH)

(*) Notice: Subject to any disclaimer, the term of this patent is extended or adjusted under 35 U.S.C. 154(b) by 72 days.

(21) Appl. No.: 16/637,401

(22) PCT Filed: Jul. 26, 2018

(86) PCT No.: PCT/EP2018/070245
§ 371 (c)(1),
(2) Date: Feb. 7, 2020

(87) PCT Pub. No.: WO2019/030002
PCT Pub. Date: Feb. 14, 2019

(65) Prior Publication Data
US 2020/0190430 A1    Jun. 18, 2020

(30) Foreign Application Priority Data

Aug. 11, 2017 (EP) .................... 17185991

(51) Int. Cl.
*C11C 3/00* (2006.01)
*A23D 9/02* (2006.01)
*C07C 29/136* (2006.01)
*C07C 29/132* (2006.01)

(52) U.S. Cl.
CPC ............ *C11C 3/003* (2013.01); *A23D 9/02* (2013.01); *C07C 29/132* (2013.01); *C07C 29/136* (2013.01)

(58) Field of Classification Search
CPC ......... C11B 3/003; A23D 9/02; C07C 29/132; C07C 29/136
See application file for complete search history.

(56) References Cited

U.S. PATENT DOCUMENTS

| | | | | |
|---|---|---|---|---|
| 6,034,130 A | * | 3/2000 | Wang | A23D 9/00 514/558 |
| 6,090,598 A | * | 7/2000 | Yamaguchi | C12P 7/6454 426/607 |
| 6,297,279 B1 | * | 10/2001 | Wang | A23C 11/04 514/558 |
| 8,153,407 B2 | * | 4/2012 | Schweitzer | A23D 9/00 435/134 |

FOREIGN PATENT DOCUMENTS

| | | | | |
|---|---|---|---|---|
| CN | 103952448 | | 7/2014 | |
| CN | 103952448 A | * | 7/2014 | ............... C12P 7/46 |

OTHER PUBLICATIONS

CN 103952448, Yang Lirong et al., Method for directionally preparing 1,3-dioleoyl-2-palmitoyl triglyceride by utilizing enzyme chemistry method, English translation, 21 pages (Year: 2014).*
Bentley et al. "An Efficient Synthesis of Symmertrical 1,3-Diglycerides" J. Org. Chem., 1970, vol. 35, No. 6, pp. 2082-2083.
Obika et al. "Symmetrical Cationic Triglycerides: An Efficient Synthesis and Application to Gene Transfer" Bioorganic & Medicinal Chemistry, 2001, vol. 9, pp. 245-254.
Morrisett, Joel D. "Synthesis of Spin0-Labeled Neutral Lipids: Nitrosyl Derivatives of Triglycerides and Sterol Esters" Lipids, 1974, vol. 9. No. 9, pp. 726-728.
Wang et al. "Chemoenzymatic synthesis of 1,3-dioleoyl-2-palmitolyglycerol" Biotechnol Lett, 2015, vol. 37, pp. 691-696.

* cited by examiner

*Primary Examiner* — Yate' K Cutliff
(74) *Attorney, Agent, or Firm* — K&L Gates LLP

(57) ABSTRACT

The present invention concerns a highly selective process for the preparation of an ingredient comprising 1,3-Olein-2-palmitin (OPO), a triglyceride present in human breast milk. The present invention also relates to 1,3-Olein-2-palmitin (OPO) ingredient obtainable by the process.

13 Claims, No Drawings

SYNTHESIS OF 1,3-OLEIN-2-PALMITIN (OPO)

CROSS REFERENCE TO RELATED APPLICATIONS

The present application is a National Stage of International Application No. PCT/EP2018/070245, filed on Jul. 26, 2018, which claims priority to European Patent Application No. 17185991.1, filed on Aug. 11, 2017, the entire contents of which are being incorporated herein by reference.

FIELD OF THE INVENTION

The present invention concerns a highly selective process for the preparation of an ingredient comprising 1,3-Olein-2-palmitin (OPO), a triglyceride present in human breast milk. The present invention also relates to the 1,3-Olein-2-palmitin (OPO) ingredient obtainable by such process wherein the ratio of OPO to POO in total TAG is equal or higher than 90:10.

BACKGROUND OF THE INVENTION

Triacylglycerols (TAG) are the major lipids found in human milk at about 39 g/L and they present a peculiar regio-specific distribution of fatty acids. The regio-specific distribution of TAG contributes to the nutritional benefits of human milk such as to fatty acid and calcium absorption and their related benefits such as gut comfort.

Infant formula (IF) ingredient design is generally aimed at structural and functional homology with respect to human milk composition and benefits.

With existing ingredients and current technologies, deriving from plants (vegetable oils) or animals (milk fat), it is at the moment not possible to replicate the TAG composition of human milk. In particular, the access to edible ingredients consisting of pure 1,3-olein-2-palmitin (OPO, CAS number: 1716-07-0) or to edible ingredients consisting of highly pure 1,3-olein-2-palmitin characterized by marginal presence of 1,2-olein-3-palmitin and/or 1-palmitin-2,3-olein (POO) is not at the moment available and would be particularly beneficial to this purpose.

The use of such ingredients in infant formulas would in fact enable preparation of lipid compositions close to human milk fats, in particular matching its level of palmitic acid in sn-2 position, which amounts to about 70% of total palmitic acid in TAG.

The selectivity OPO/POO in available ingredients enriched in OPO seems to be of particular relevance as the POO species (POO+OOP) can be hardly removed by purification processes which are industrially applicable and its presence contributes to lower the amount of palmitic acid at the sn-2 position, thus going in the opposite direction.

Currently, OPO enriched ingredients are already incorporated into some IF. They are produced using enzymatic reactions (like for example Betapol® or Infat®) but the OPO content in these ingredients ranges from 20 to 28% w/w of total TAG, the rest being other TAG (for example POO which may range from 5 to 8% w/w of total TAG). The low OPO content of these ingredients coupled with presence of other TAG represents a limit for their use in the preparation of IF having a fat portion reproducing as far as possible the fat content of human breast milk.

Other OPO syntheses are also known and described in the literature on lab scale using enzymatic reactions. These reactions are anyway either not possible to scale up at an industrial level (due to complex purification steps to be performed to get to the desired OPO content and/or selectivity over other TAG) or they are not capable to deliver an ingredient with desired OPO content and/or selectivity over other TAG.

Accordingly, it is an objective of the present invention to provide a process for the preparation of an OPO ingredient characterized by a high level of purity and/or selectivity over other TAG, in particular over POO.

It would be particularly advantageous to provide a process for the preparation of an OPO ingredient wherein the ratio of OPO to POO in total TAG would be equal or higher than 90:10. Even more advantageously, it would be interesting to provide a process for the preparation of an OPO ingredient characterized by a palmitic acid content at sn-2 position higher than 70% of total palmitic content and wherein the ratio of OPO to POO in total TAG would be equal or higher than 90:10.

SUMMARY OF THE INVENTION

It has been surprisingly found that the above mentioned technical problem may be solved by the process described in the present invention.

In one aspect of the present invention, a process for the preparation of an OPO ingredient is provided which comprises the following step:

b) subjecting 2-oxopropane-1,3-diyl dioleate to reduction reaction in a solvent system comprising THF and in the presence of Sodium Borohydride to yield 2-hydroxypropane-1,3-diyl dioleate.

In another aspect of the present invention, an OPO ingredient obtainable by the process of the present invention is provided, such OPO Ingredient being characterized by a ratio of OPO to POO equal or higher than 90:10.

Definitions

Within the context of the present invention the term "OPO" refers to 1,3-Olein-2-palmitin and/or 2-(palmitoyloxy)propane-1,3-diyl dioleate and/or (2-(Palmitoyloxy)-1,3-propanediyl (9Z,9'Z)bis(-9-octadecenoate) (CAS number: 1716-07-0)

Within the context of the present invention the term "POO" refers to both 3-(Palmitoyloxy)-1,2-propanediyl (9Z,9'Z)bis(-9-octadecenoate), (OOP, CAS number: 14960-35-1), and/or 1-(Palmitoyloxy)-2,3-propanediyl (9Z,9'Z)bis(-9-octadecenoate), (POO, CAS number: 14863-26-4). It is to be noted that when reference is made to amounts of "POO", this also includes amounts of OOP present in the ingredient.

Within the context of the present invention, the terms "ratio of OPO to POO in total TAG" and/or "ratio of OPO to POO" and/or "ratio OPO/POO" and/or "selectivity OPO to POO" and/or "selectivity OPO/POO" indicate the weight ratio between amounts of OPO to POO in total TAG normalized to 100 parts.

As it will be apparent to the person skilled in the art, an exemplary calculation of such ratio/selectivity is hereby provided based on imaginary OPO and POO contents in total TAG:

OPO Content in total TAG: 45 g/100 g total TAG
POO Content in total TAG: 6 g/100 g total TAG
OPO Content normalized to 100 parts: 88.2 [calculated from 45:51=X:100 thus X=(45/51)×100]
Ratio of OPO to POO in total TAG: 88.2:11.8

Within the context of the present invention, the term "OPO Ingredient" or "OPO enriched Ingredient" or "1,3-Olein-2-palmitin ingredient" or simply "OPO" identifies an edible ingredient comprising 1,3-Olein-2-palmitin (OPO) characterized by a palmitic acid content as sn-2 position higher than 70% of total palmitic content and wherein the ratio of OPO to POO in total TAG would be equal or higher than 90:10.

Within the context of the present invention, the term "solvent system" identifies a mixture of one or more solvents which is used to perform one or more reaction step according to the present invention.

The present invention will now be described in more detail in the following detailed description of the invention.

DETAILED DESCRIPTION OF THE INVENTION

The Process

In one embodiment, the process according to the present invention provides a selectivity OPO to POO in the deriving product equal or higher than 90:10.

In another embodiment, the process according to the present invention provides an OPO ingredient characterized by a palmitic acid content at sn-2 position higher than 70% of total palmitic content and by a ratio of OPO to POO equal or higher than 90:10.

In one embodiment of the present invention, a process for the preparation of an OPO ingredient is provided which comprises the following steps:

a) reacting 1,3-dihydroxyacetone with oleic acid or oleoyl chloride to yield to the 2-oxopropane-1,3-diyl dioleate;

b) subjecting 2-oxopropane-1,3-diyl dioleate to reduction reaction in a solvent system comprising THF and in the presence of Sodium Borohydride to yield 2-hydroxypropane-1,3-diyl dioleate.

In another embodiment of the present invention, a process for the preparation of an OPO ingredient is provided which comprises the following steps:

b) subjecting 2-oxopropane-1,3-diyl dioleate to reduction reaction in a solvent system comprising THF and in the presence of Sodium Borohydride to yield 2-hydroxypropane-1,3-diyl dioleate;

c) reacting 2-hydroxypropane-1,3-diyl dioleate with palmitoyl chloride to yield 1,3-Olein-2-palmitin.

Scheme 1 reports the synthetic reaction scheme according to one embodiment of the present invention:

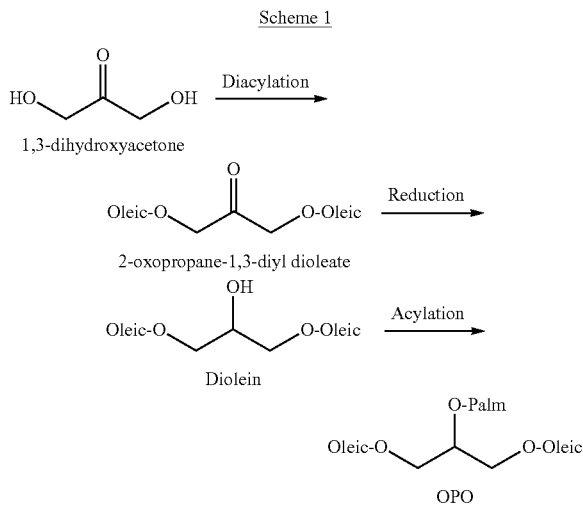

In one embodiment, the process for the preparation of an OPO ingredient according to the present invention is based on the synthetic approach depicted in Scheme 1. In such embodiment of the present invention, a process for the preparation of an OPO ingredient is provided which comprises the following steps:

a) reacting 1,3-dihydroxyacetone with oleic acid or oleoyl chloride to yield to the 2-oxopropane-1,3-diyl dioleate;

b) subjecting 2-oxopropane-1,3-diyl dioleate to reduction reaction in a solvent system comprising THF and in the presence of Sodium Borohydride to yield 2-hydroxypropane-1,3-diyl dioleate;

c) reacting 2-hydroxypropane-1,3-diyl dioleate with palmitoyl chloride to yield 1,3-Olein-2-palmitin.

Step a): Diacylation of 1,3-dihydroxyacetone

The process according to the present invention may advantageously start by the diacylation of the 1,3-dihydroxyacetone with oleic acid or oleoyl chloride to yield to the 2-oxopropane-1,3-diyl dioleate.

In one embodiment of the present invention, this transformation can be performed by reacting 1,3-dihydroxyacetone with oleic acid using either coupling agents (e.g. carbodiimide with DMAP), typically at room temperature, or enzymes (esterases, such as for example Novozym® 435 or Lipozyme RM IM) at temperatures ranging from 30° C. to 60° C.

In another embodiment of the present invention, the diacylation can be performed by reacting 1,3-dihydroxyacetone with oleoyl chloride in the presence of pyridine or pyridine derivatives (e.g. 2,6-lutidine) at temperatures ranging from 0° C. to room temperature, for example at a temperature of 0° C.

In one embodiment of the present invention, several aprotic solvents can be used to perform step a) such as, for example: DMF, THF, CHCl3, CH2Cl2, MTBE, MeCN. In one embodiment, the aprotic solvent used to perform step a) is CHCl3.

Step b): Reduction to 1,3-Di(cis-9-octadecenoyl)glycerol (1,3-diolein)

In step b), the intermediate ketone (1a) is reduced to 1,3-Di(cis-9-octadecenoyl)glycerol in the presence of sodium borohydride. The conditions described in the literature for this type of reaction (S. Obika et al., Bioorg. Med. Chem. 2001, 9, 245-254) lead to 67-76% ratio of OPO vs its isomer POO in the final OPO ingredient which originated from low selectivity Of 1,3 vs 1,2-diolein obtained in step b) (assessed by HPLC-ELSD).

The present inventors have surprisingly identified appropriate operating conditions which allowed much higher selectivity (higher than 95:5 as indicated in the examples). It is believed that step b) plays a critical role in the determination of what will be OPO/POO selectivity in the final OPO ingredient.

In the framework of such reaction step in fact formation of 1,3-diolein takes place which will lead to the desired OPO ingredient after acylation with a palmitic residue [step c) according to the present invention]. Anyway, as a by product of step b), 1,2-diolein may also be formed during the reduction step by migration of one oleic residue; such 1,2-diolein species, which proves to be almost impossible to be separated from 1,3-diolein by standard chromatographic techniques, is responsible for the formation of the undesired POO impurity after acylation with palmitic residue. On such basis, formation of by-product 1,2-diolein should be avoided as much as possible in the context of step b) of the process of the present invention.

Without wishing to be bound by theory, it is believed that such by product formation is avoided by minimizing contact of diolein obtained in step b) with water.

In one embodiment, step b) is carried out under anhydrous conditions.

In one embodiment, step b) is carried out in THF or in a mixture of THF/MeOH or THF/EtOH.

In one embodiment, anhydrous THF alone or in combination with anhydrous MeOH or EtOH or combinations thereof is used as solvent for step b).

In one embodiment, step b) (reduction reaction) is performed at a temperature lower than room temperature, for example zero degree. Temp lower than room temperature, for example at zero degree C.

In another embodiment, step b) (work up) is performed at a temperature lower than room temperature, for example zero degrees. Temp lower than room temperature, for example at zero degree C.

In a still further embodiment, step b) (reduction reaction and work up) is performed at a temperature lower than room temperature, for example zero degree. Temp lower than room temperature, for example at zero degree C.

In one embodiment, work up of the reaction (i.e. quench of reagents once the desired reaction is finished) is designed to avoid that diolein gets in contact with acidic water. In such embodiment, THF (or its mixture with MeOH and/or EtOH) is partially removed and another solvent which is not miscible with water—for example chloroform—is added before the addition of acidulated water is performed to the reaction mixture to inactivate Sodium Borohydride and then the organic phase is separated and the diolein recovered by evaporation of the organic solvent.

In another embodiment, no purification is performed on the diolein obtained in step b). Without wishing to be bound by theory, it is believed that such approach further avoids the occurrence of oleic residue migration and consequent lowering of the selectivity.

In a still further embodiment, storage of 1,3-diolein obtainable from step b) is performed a temperature lower or equal to room temperature (for example at a temperature lower than 0° C.), and/or in the absence of direct light and/or in a controlled atmosphere where oxygen is not present and/or for not prolonged storage times (for example no longer than 2 days). In another embodiment, the 1,3-diolein obtainable from step b) is shortly reacted according to step c) of the present invention. Without wishing to be bound by theory, it is believed that such approaches further avoids the occurrence of oleic residue migration and consequent lowering of the selectivity.

Step c): Preparation of 1,3-Olein-2-palmitin

Finally, 2-hydroxypropane-1,3-diyl dioleate may be acylated with a palmitic residue.

In one embodiment, this transformation can be performed by reacting diolein obtainable from step b) with palmitic acid using either coupling agents (e.g. carbodiimide with DMAP), typically at room temperature, or enzymes (esterases like Novozym® 435 or Lipozyme RM IM) at temperatures ranging from 30° C. to 60° C.

In another embodiment of the present invention, the acylation can be performed by reacting diolein with palmitoyl chloride in the presence of pyridine or pyridine derivatives (e.g. 2,6-lutidine) at temperatures ranging from 0° C. to room temperature, for example at a temperature of 0° C. or at room temperature.

In one embodiment of the present invention, several aprotic solvents can be used such as, for example: DMF, THF, CHCl3, CH2Cl2, MTBE, MeCN, hexane. In one embodiment, the aprotic solvent used to perform step c) is CHCl3.

The above described conditions can yield OPO with OPO/POO selectivity higher than 95:5 (i.e. <5% of POO).

OPO Ingredient

According to one embodiment of the present invention, an OPO Ingredient is provided comprising 1,3-Olein-2-palmitin (OPO) and characterized by a palmitic acid content at sn-2 position higher than 70% of total palmitic content and by a ratio of OPO to POO equal or higher than 90:10.

In one embodiment, for the OPO ingredient of the present invention the palmitic acid content at sn-2 position is equal or higher than 75% of total palmitic content, for example equal or higher than 80% of total palmitic content.

In another embodiment, for the OPO ingredient of the present invention the weight ratio of OPO to POO is equal or higher than 92:8, for example equal or higher than 95:5, for example 98:2.

In another embodiment, for the OPO ingredient of the present invention the palmitic acid content at sn-2 position is equal or higher than 75% of total palmitic content, for example equal or higher than 80% of total palmitic content and the weight ratio of OPO to POO is equal or higher than 92:8, for example equal or higher than 95:5.

In one embodiment of the present invention, the OPO ingredient may be used as a food ingredient.

The access to this OPO ingredient allows to formulate a lipid composition very similar to the one found in human milk and suitable for the preparation of infant nutrition product.

Several embodiments and aspects of the present invention are herebelow provided:

A). A process for the preparation of an OPO ingredient comprising the following step:

b) subjecting 2-oxopropane-1,3-diyl dioleate to reduction reaction in a solvent system comprising THF and in the presence of Sodium Borohydride to yield 2-hydroxypropane-1,3-diyl dioleate.

B). A process according to embodiment A) which also comprises:

a) reacting 1,3-dihydroxyacetone with oleic acid or oleoyl chloride to yield to the 2-oxopropane-1,3-diyl dioleate.

C). A process according to embodiments A) or B) which also comprises:

c) reacting 2-hydroxypropane-1,3-diyl dioleate with palmitoyl chloride to yield 1,3-Olein-2-palmitin.

D). A process according to anyone of embodiments A) to C) wherein step a) is performed by reacting in chloroform 1,3-dihydroxyacetone with oleoyl chloride in the presence of pyridine or pyridine derivatives (e.g. 2,6-lutidine) at temperatures ranging from 0° C. to room temperature, for example at a temperature of 0° C.

E). A process according to anyone of embodiments A) to D) wherein step b) is carried out under anhydrous conditions in a solvent system comprising THF.

F). A process according to anyone of embodiments A) to E) wherein step b) is carried out under anhydrous conditions in a solvent system consisting of THF or THF/MeOH or THF/EtOH or THF/MeOH/EtOH.

G). A process according to anyone of embodiments A) to F) wherein step b) is performed at a temperature lower than room temperature, for example zero degree. Temp lower than room temperature, for example at zero degree C.

H). A process according to anyone of the preceding embodiments wherein in the work up of step b) the solvent system comprising THF is partially removed and replaced with a solvent which is not miscible with water, for example chloroform, addition of acidulated water is performed to the reaction mixture to inactivate Sodium Borohydride, the organic phase is separated and the diolein recovered by evaporation of the organic solvent.

J). A process according to anyone of embodiments A) to C) wherein step a) is performed by reacting in chloroform 1,3-dihydroxyacetone with oleoyl chloride in the presence of pyridine or pyridine derivatives (e.g. 2,6-lutidine) at temperatures ranging from 0° C. to room temperature, for example at room temperature.

K). An OPO ingredient characterized by a palmitic acid content as sn-2 position higher than 70% of total palmitic content and by a ratio of OPO to POO equal or higher than 90:10.

L). An OPO ingredient according to embodiment K) wherein the palmitic acid content at sn-2 position is equal or higher than 75% of total palmitic content, for example equal or higher than 80% of total palmitic content.

M). An OPO ingredient according to embodiments K) or L) wherein the weight ratio of OPO to POO is equal or higher than 92:8, for example equal or higher than 95:5.

N). An OPO ingredient according to anyone of embodiments K) to N) which is obtainable by the process as described in anyone of embodiments A) to J).

Experimental Section

Abbreviations:
HPLC: high performance liquid chromatography
FWHM: full width at half maximum
MS: mass spectrometer
THF=tetrahydrofurane
AcOEt=Ethyl Acetate
MeOH=methanol
EtOH=ethanol
$CHCl_3$=chloroform
$CH_2Cl_2$=methylene chloride
Room temperature=RT=25° C.
DMF=N,N-dimethylformamide
MTBE=methyl-t-butyl ether
MeCN=acetonitrile
DMAP=4-dimethylaminopyridine Analytical Methods:

Method A:

This method exploits the advantages of hybrid mass spectrometry for the mapping, identification and quantification of TAG regioisomers in fats and oils and finished products. The identification is performed based on the accurate mass (better than 1 ppm), adduct envelope and fragmentation pattern obtained by data-dependent fragmentation. Quantification was based on the high resolution ion chromatograms, while relative proportion of sn-1(3)/sn-2 regioisomers was calculated based on generalized fragmentation models and the relative intensities observed in the product ion spectra.

Sample Preparation

Oil/fat samples are solubilized in n-hexane. Next, 100 μL of this solution were added to 900 μL acetone:methanol 4:1. Finally, 50 μL aliquot of this latter solution along with 250 μL stable isotope labeled internal standard solution (400 picomoles/mL) was transferred into new glass vial and 700 μL acetone:methanol 4:1 were added. A 10 μL aliquot was injected for analysis.

Equipment

A HPLC equipped with an Agilent Poroshell 120 EC-C18 column (2.7 μm particle size, 2.1×250 mm, from BGB Analytix, Boeckten, Switzerland, cat. no. 693775-902) was used for separation of analytes. An Orbitrap elite velos hybrid mass spectrometer (ThermoFisher Scientific, Bremen, Germany) was used for mass analysis, fragmentation and quantification of the TAG.

HPLC Conditions

Solvent A was 1 mM ammonium-formate and 2 μM sodium-formate solubilized in methanol, whereas solvent B was isopropanol:n-hexane 1:1.

The gradient was as following: 0-3 min isocratic 100% A at 600 μL/min; 3-53 min gradient to 70% A at 600 μL/min; 53-60 min gradient to 5% A and to 400 μL/min; 60-70 min isocratic 5% A at 400 μL/min; 70-73 min gradient to 100% A and to 600 μL/min; 73-80 min equilibrate at 100% A at 600 μL/min.

Mass Spectrometer Conditions

Electrospray ionization (ESI) in positive ion mode was employed to form ions at 300° C. nebulizer temperature and 5 kV capillary voltage. Nebulizer and auxiliary gases were nitrogen at 40 and 20 units respectively. Tube lens was adjusted to 110 V, ion accumulation time for Fourier transform detection was 100 ms. Other parameters were the typical values optimized during calibration. The Orbitrap was operated at 30,000 FWHM resolution (full width at half maximum) in an m/z 100-2000 range. Data dependent events were triggered according to an inclusion list containing the accurate masses of ammoniated TAG, applying parent mass width criteria of ±5 ppm. Inclusion list criterion for data-dependent acquisition was established in MS Office Excel by calculating the elemental composition and corresponding accurate mass for TAG obtained by the combination of the 40 most common FA on the glycerol backbone. The combination of these FA yields approximately 40,000 TAG: these species can be detected and identified using the herein described method. Additional mass tagging of m/z 4.95540 (difference between ammoniated and sodiated adducts) was applied in a parent intensity range of 0-100%. Intensity threshold was 100,000 cps, preview mode for FT-MS master scans was enabled. Precursor ion isolation, fragmentation and detection was performed in the linear ion trap. Only the ammoniated adducts (low mass partner) were fragmented.

Accumulation time for parent ions was 50 ms, isolation width was m/z 3, normalized collision energy 30%, activation Q value was 0.250, activation time was 30 ms. Please note, that in the case of ammoniated TAG the above specified isolation width yielded the unit isolation of parent ions and complete elimination of isotopomers. Using a dynamic exclusion list and 30 s exclusion time, ten data dependent events were triggered per two scan cycles (5 fragmentation events per one scan cycle). The dynamic exclusion parameters were: repeat count 1; repeat duration 0 s; exclusion list size 25; exclusion duration 2.5 s; exclusion mass width±5 ppm.

Intermediate 1a: Preparation of
2-oxopropane-1,3-diyl dioleate (Step a)

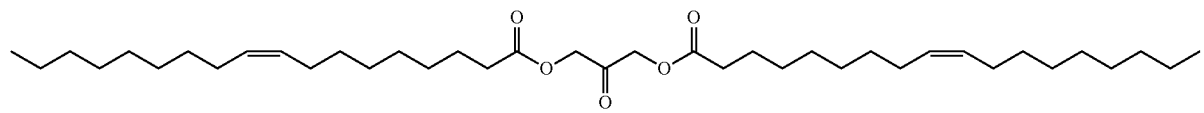

1a

Method 1

Pyridine (9.79 ml, 121.5 mmol) was added to a suspension of 1,3-dihydroxyacetone (5 g, 55.5 mmol) in 450 ml of chloroform. After 5 min, oleoyl chloride (33.3 g, 111.1 mmol) was added dropwise under stirring at 0° C. then 48 h at room temperature. The solution was diluted in 450 ml of chloroform, washed with water (500 ml), aqueous sodium bicarbonate (500 ml) and brine (500 ml), dried over anhydrous sodium sulfate, and the solvent evaporated under vacuum to get crude residue of 1a. The crude was purified by recrystallization: the residue was dissolved in 150 ml of methanol (5 vol.) and allowed to stand for 48 h at 0° C. The excess methanol was decanted out to get the pure product (5.3 g) as a white solid. The methanol filtrate was then concentrated and same procedure was applied to get another 4.8 g of pure compound. This second methanol filtrate was still containing the desired product but it was not recrystallized again.

Method 2

Oleic acid (3.13 g, 11.10 mmol) and 4-DMAP (1.36 g, 11.10 mmol) were added to a suspension of 1,3-dihydroxyacetone (0.5 g, 5.55 mmol) in 10 ml of chloroform. A solution of DCC (11.10 mmol) in 2 ml of chloroform was then added dropwise under stirring at room temperature. After completion of reaction (overnight), the precipitated dicyclohexylurea was removed by filtration and the solvent reduced under vacuum (rotavapor). The residue was purified by silica gel column chromatography, 8 to 10% EtOAc in hexane, to give 2-oxopropane-1,3-diyl dioleate (1.7 g, 49.5% yield).

Intermediate 1b: Preparation of
2-hydroxypropane-1,3-diyl dioleate (Step b)

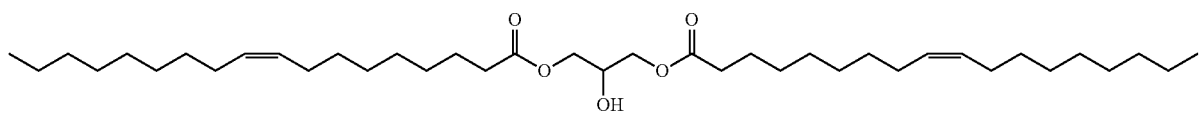

1b 2-oxopropane-1,3-diyl dioleate 1a (2.0 g, 3.23 mmol) was dissolved in THF (250 ml). The reaction mixture was cooled at 20-25° C., and sodium borohydride (0.119 g, 3.23 mmol) was carefully added portionwise. After 30 min, the solution was evaporated to half under vacuum at 30° C. and it was diluted with 100 ml of chloroform. Then water (50 ml) was added. Excess borohydride was neutralized by dropwise addition of glacial acetic acid (~0.5 ml, up to pH 5-6). The organic layer was washed with water (50 ml), aqueous sodium bicarbonate (50 ml) and brine (50 ml), dried over anhydrous sodium sulfate, and the solvent evaporated under vacuum to yield product 1b (2.0 g, quantitative yield).

Example 1c: Preparation of 1,3-Olein-2-palmitin
(Step c)

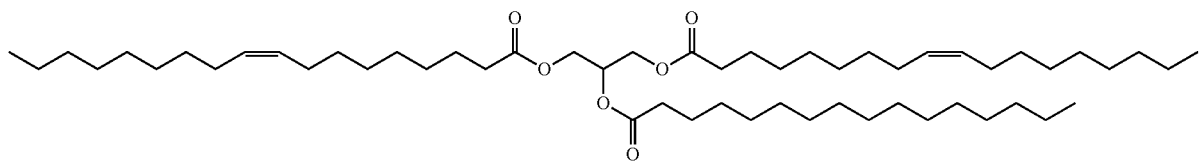

1c

Method 1

Pyridine (1.29 ml, 16.1 mmol) was added to a suspension of 2-hydroxypropane-1,3-diyl dioleate (2.0 g, 3.22 mmol) in 60 ml of chloroform. After 5 min stirring at room temperature, palmitoyl chloride (4.41 g, 16.1 mmol) was added dropwise. The reaction mixture was stirred at room temperature for 16 h. The solution was then diluted in 50 ml of chloroform, washed with water (50 ml), dil. HCl solution, aqueous sodium bicarbonate (25 ml) and brine (50 ml), dried over anhydrous sodium sulfate, and the solvent evaporated under vacuum to furnish residue of 1c. Residue was purified by silica gel column chromatography (eluant: EtOAc/hexane 1%) to give product 1c (3.2 g, 87% yield). It was then triturated with methanol to get 1.1 g of OPO.

Method 2:

Diolein 1b (1.0 g, 1.61 mmol) was dissolved in 5 ml DCM. Then EDC.HCl (0.37 g, 1.93 mmol) and DMAP (40 mg, 0.32 mmol) were added at room temperature. After 5 min. of stirring, palmitic acid (0.54 g, 1.90 mmol) was added to reaction mixture. After completion of the reaction, the reaction mixture was diluted in 20 ml of DCM, washed with water (50 ml), dil. HCl solution, aqueous sodium bicarbonate (50 ml) and brine (50 ml). The organic layer was dried over anhydrous sodium sulfate and concentrated under vacuum to get residue of 1c. The residue was purified by silica gel column chromatography, 2 to 5% EtOAc in hexane to give OPO (1.0 g, 72% yield).

Method 3:

Diolein (124 mg, 0.2 mmol) and palmitic acid (102 mg, 0.4 mmol) were poured into a vial then solubilized with 2 mL of dry hexane. 12 mg of enzymes (Novozym® 435) and molecular sieves 4A were added and the closed vial was heated at 60° C. under stirring for 16 h. After completion, OPO was then obtained after filtration and purification on silica gel column chromatography.

Example 2: Analytical Characterization on OPO Ingredient According to the Invention and Comparison with Commercially Available Ingredients Containing OPO In order to assess the identity and amounts of TAG and fatty acids present in the OPO Ingredient according to the present invention and to compare the ingredient with commercially available products enriched in OPO, an analytical characterization of three samples was carried out according to the method A above described.

The results obtained in this experiment are reported in Table 1 below:

TABLE 1

| Ingredient | Palmitic residues in sn-2 position over total palmitic [g/100 g palmitic acid] | OPO Content [g/100 g total TAG] | POO Content [g/100 g total TAG] | OPO:POO ratio |
|---|---|---|---|---|
| Example 1c | 94.92 | 87.4 | 1.01 | 98.85:1.15 |
| Betapol ® | 56.9 | 27.96 | 5.64 | 83.2:16.8 |
| InFat ® | 55.4 | 19.87 | 7.85 | 71.7:28.3 |

Based on the results reported above, the OPO ingredient prepared according to the process of the present invention clearly differentiates with respect to other commercially available OPO enriched ingredients. Of note, the palmitic acid content at sn-2 position is remarkably higher, as well as the OPO content and OPO:POO selectivity.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention claimed is:

1. A process for preparation of a 1,3-Olein-2-palmitin ingredient, the process comprising:
   subjecting 2-oxopropane-1,3-diyl dioleate to a reduction reaction under an anhydrous condition in a solvent system comprising tetrahydrofurane and in the presence of sodium borohydride to yield 2-hydroxypropane-1,3-diyl dioleate;
   partially removing and replacing the tetrahydrofurane with a solvent which is not miscible with water;
   adding acidulated water to inactivate the sodium borohydrate to form an inactivated mixture;
   separating an organic phase of the inactivated mixture;
   evaporating the solvent to recover the 2-hydroxypropane-1,3-diyl dioleate; and
   reacting the 2-hydroxypropane-1,3-diyl dioleate with palmitoyl chloride to yield the 1,3-Olein-2-palmitin.

2. The process according to claim 1 comprising:
   reacting 1,3-dihydroxyacetone with oleic acid or oleoyl chloride to yield the 2-oxopropane-1,3-diyl dioleate.

3. The process according to claim 1 comprising reacting 1,3-dihydroxyacetone in chloroform with oleoyl chloride in the presence of 2,6-lutidine at a temperature ranging from 0° C. to 25° C. to yield the 2-oxopropane-1,3-diyl dioleate.

4. The process according to claim 1, wherein the solvent system consists of the tetrahydrofurane.

5. The process according to claim 1, wherein the solvent system is selected from the group consisting of the tetrahydrofurane, the tetrahydrofurane/MeOH, the tetrahydrofurane/EtOH, and the tetrahydrofurane/MeOH/EtOH.

6. The process according to claim 1, wherein the reduction reaction is performed at a temperature lower than 25° C.

7. The process according to claim 1 comprising reacting 1,3-dihydroxyacetone in chloroform with oleoyl chloride in the presence of pyridine or a pyridine derivative at a temperature ranging from 0° C. to 25° C. to yield the 2-oxopropane-1,3-diyl dioleate.

8. A 1,3-Olein-2-palmitin ingredient comprising a palmitic acid content at sn-2 position greater than 70% of a total palmitic content and by having a weight ratio of 1,3-Olein-2-palmitin to 3-(Palmitoyloxy)-1,2-propanediyl (9Z,9′Z)bis(-9-octadecenoate) or to 1-(Palmitoyloxy)-2,3-propanediyl (9Z,9′Z)bis(-9-octadecenoate) equal or higher than 90:10.

9. The 1,3-Olein-2-palmitin ingredient according to claim 8, wherein the palmitic acid content at sn-2 position is equal or greater than 75% of the total palmitic content.

10. The 1,3-Olein-2-palmitin ingredient according to claim 8, wherein the weight ratio of the 1,3-Olein-2-palmitin to the 3-(Palmitoyloxy)-1,2-propanediyl (9Z,9′Z)bis(-9-octadecenoate) or to the 1-(Palmitoyloxy)-2,3-propanediyl (9Z,9′Z)bis(-9-octadecenoate) is equal or greater than 92:8.

11. The 1,3-Olein-2-palmitin ingredient according to claim 8, wherein the weight ratio of the 1,3-Olein-2-palmitin to the 3-(Palmitoyloxy)-1,2-propanediyl (9Z,9′Z)bis(-9-octadecenoate), or to the 1-(Palmitoyloxy)-2,3-propanediyl (9Z,9′Z)bis(-9-octadecenoate) is equal or greater than 95:5.

12. The 1,3-Olein-2-palmitin ingredient according to claim 8, wherein the weight ratio of the 1,3-Olein-2-palmitin to the 3-(Palmitoyloxy)-1,2-propanediyl (9Z,9'Z)bis(-9-octadecenoate) or to the 1-(Palmitoyloxy)-2,3-propanediyl (9Z,9'Z)bis(-9-octadecenoate) is equal or greater than 98:2.

13. The 1,3-Olein-2-palmitin ingredient according to claim 8, wherein the palmitic acid content at sn-2 position is equal or greater than 80% of the total palmitic content.

\* \* \* \* \*